United States Patent [19]

Prota et al.

[11] Patent Number: 5,435,810
[45] Date of Patent: Jul. 25, 1995

[54] HAIR DYEING PROCESS WITH AMINOALKYLTHIO SUBSTITUTED DIHYDROXYBENZENE AND OXIDATIVE AGENTS

[75] Inventors: Guiseppe Prota, Naples, Italy; Gottfried Wenke, Woodbridge, Conn.

[73] Assignee: Clairol Incorporated, Stamford, Conn.

[21] Appl. No.: 174,486

[22] Filed: Dec. 27, 1993

[51] Int. Cl.$^6$ .............................................. A61K 7/13
[52] U.S. Cl. .................................. 8/406; 8/407; 8/408; 8/424; 8/587
[58] Field of Search ............... 8/405, 406, 407, 408, 8/424, 587

[56] References Cited

U.S. PATENT DOCUMENTS

| | | | |
|---|---|---|---|
| 4,776,857 | 10/1988 | Carroll et al. | 8/406 |
| 4,968,497 | 11/1990 | Wolfram et al. | 8/408 |
| 5,131,911 | 7/1992 | Lang et al. | 8/405 |
| 5,240,715 | 8/1993 | Ahene et al. | 424/574 |
| 5,273,550 | 12/1993 | Prota et al. | 8/405 |
| 5,279,617 | 1/1994 | Prota et al. | 8/406 |
| 5,279,618 | 1/1994 | Prota et al. | 8/406 |

*Primary Examiner*—Paul Lieberman
*Assistant Examiner*—Caroline L. Dusheck
*Attorney, Agent, or Firm*—Charles J. Zeller

[57] ABSTRACT

A process of dyeing hair by preparing and applying to the hair an aqueous reaction medium comprising an aminoethanethio substituted dihydroxybenzene and a periodate, iodate, ferricyanide or persulfate oxidizing agent, the composition optionally containing a color modifier selected from the group consisting of direct dyes, primary intermediates, couplers, cysteine, dopa species and mixtures thereof, additionally containing a buffer to maintain the pH in the range from 2 to 11 during the oxidation reaction; and removing the aqueous reaction medium from the hair after formation of the desired color and compositions and kits for practicing such processes. The reaction medium may be formed by simultaneous addition of the dihydroxybenzene and the oxidant to the hair or by addition of the dihydroxybenzene followed by addition of the oxidant.

13 Claims, No Drawings

HAIR DYEING PROCESS WITH AMINOALKYLTHIO SUBSTITUTED DIHYDROXYBENZENE AND OXIDATIVE AGENTS

FIELD OF THE INVENTION

This invention relates to compositions, methods and kits for dyeing hair. More specifically, the invention relates to methods of dyeing hair in which mixtures of certain dihydroxybenzenes which are substituted with selected aminoethanethio substituents are oxidized to produce phaeomelanins, trichochromes and like compounds for coloring human hair. The invention relates also to compositions for conducting the hair dyeing process and to the packaged reactants sold in the form of a kit.

BACKGROUND OF THE INVENTION

Modern hair dyeing has developed from its initiation in the 1950's to the point where, today, it is the third largest product type in the hair category following shampoos and conditioners.

A wide variety of hair dyes or colorants have been developed, many of which involve oxidation of selected organic compounds or combinations of compounds with oxidizing agents such as hydrogen peroxide. Other known oxidizing agents for use with such compounds include perborates, persulfates, and perhalates, particularly periodates. These oxidizing agents are generally employed as ammonium salts or as salts of alkali metals. In the course of this development, it has been learned that the applicability of an oxidant to one or more oxidizable substrates does not permit the prediction that the same oxidant or an apparently similar oxidant will be useful for oxidizing another oxidizable substrate to achieve a desirable color change in human hair.

Despite the large number of hair dyeing compositions and processes which have been developed, the art is constantly searching for methods and compositions to improve the efficiency of the hair coloring process, decrease the time required, impart desirable tints and tones to the hair and avoid the use of hydrogen peroxide, which may be damaging to the hair or to the skin which it contacts.

BRIEF SUMMARY OF THE INVENTION

It has now been found that an aqueous hair dyeing process of selected aminoethanethio substituted dihydroxybenzenes at a pH of from about 2 to 11 can be practiced to attain highly desirable permanent tints and tones in human hair.

Among the important advantages achieved by the practice of this invention, one of the most significant is that the oxidation is accomplished without the use of hydrogen peroxide, thereby avoiding the known disadvantages of this oxidizing agent. Another is that some of the alanyl substituted compounds such as cysteinyl substituted compounds such as 3,4-dihydroxyphenylalanine and its analogs, homologs and derivatives are known intermediates in human melanogenesis. They are expected, therefore, to be toxicologically acceptable and to produce natural tones. Still another advantage is that at least some of the end products of the oxidation reaction are expected to be identical with or closely related to trichochromes or phaeomelanins, the natural red and yellow pigments. Thus, by the practice of this invention it is possible to achieve natural appearing red and yellow hair tones which have heretofore eluded the art.

The process of this invention is, so far as is known, the first practical procedure for preparing and utilizing phaeomelanin, trichochromes and like compounds under controlled conditions as hair colorants. The process thus extends melanin chemistry to natural colors other than black or brown which are the colorations achieved by oxidative procedures which produce melanin and melanin like pigments. Variations in these "melanin" colors have heretofore required the use of hair color modifiers such as couplers and/or primary intermediates. With the aminoethanethio substituted dihydroxybenzenes of this invention if it possible to achieve a whole spectrum of natural colors, and this spectrum can be appreciably extended by the use of color modifiers as explained hereinafter.

The substituted dihydroxybenzene compounds that are used in accordance with the present invention form benzothiazine and benzothiazine-like compounds by oxidative ring closure. Illustrative ring closure schemes are shown below:

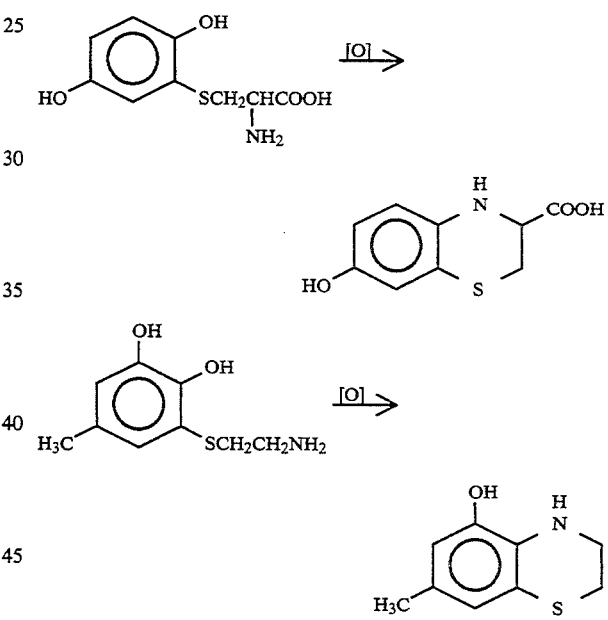

These reactions are illustrative of the initial reaction in the sequence of reactions which takes place in the conversion of the starting materials and their oxidative conversion to the coloring pigments of this invention. This is believed to be the first step in the transformation of the substituted dihyroxybenzenes of the invention to the final colored pigments which are understood to be a complex mixture of phaeomelanins, trichochrome and similar pigments. The reaction sequences by which the final pigments are formed are not completely understood.

It will be seen that the benzothiazines are formed by ring closure mechanisms which involve adjacent hydrogen atoms or hydroxyl groups. If ring closure can take place by a mechanism which involves either an adjacent hydrogen atom or an adjacent hydroxyl group, the latter will be the principal reaction. It will also be clear that some dihydroxy isomers can produce more than one benzothiazine. It is, therefore, readily apparent that the final pigment mixture can be very complex, and made even more so if the original hair coloring composition contains more than one substituted dihydroxybenzene. It will also be apparent that the compositions of the invention can be employed to achieve a wide variety of hair colors.

The substituted dihydroxybenzene compounds utilized in the methods of this invention are known or can be readily prepared from available starting materials using conventional procedures. See, for example, Gazz. Chim. Ital. 120(1), 21,1990; ibid 97(10), 1451, 1967; ibid, 98(4), 495, 1968; Experientia 33(8),1118, 1977; J. Heterocycl. Chem. 7(3), 555 (1970); Tetrahedron 46(19), 6831, 1990; and the references cited are specifically incorporated herein by reference.

Aminoethanthio substituted dihydroxybenzenes useful in the practice of the present invention are shown below:

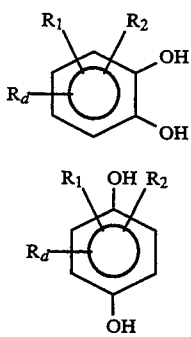

wherein $R_1$ is

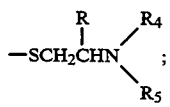

$R_d$ is

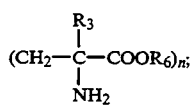

R is H or $COOR_7$; $R_2$, $R_3$, $R_4$ and $R_5$, which may be the same or different, are H, $C_1$–$C_6$ alkyl or $C_1$–$C_6$ hydroxyalkyl; $R_6$ and $R_7$, which may be the same or different, are alkali metal, H or $C_1$–$C_6$ alkyl, and n is 0 or 1.

Synthesis of the compound of Formula II wherein n=0; $R_1$ is —$SCH_2CH_2NH_2$ and $R_2$ is hydrogen is accomplished by addition of 2-aminoethanethiol to p-benzoquinone.

The compound of Formula I wherein n=0; $R_1$ is —$SCH_2CH_2NH_2$ and $R_2$ is hydrogen was prepared by aminoethylation of 1,2-dihydroxy-3mercaptobenzene. This latter compound was prepared through ferricyanide oxidation of o-dihydroxybenzene in the presence of thiourea, followed by hydrolysis.

The compound of Formula V wherein $R_1$ is —$SCH_2CH_2NH_2$ and $R_2$ is hydrogen was achieved by addition of 2-aminoethanethiol to o-benzoquinone.

Other compounds represent by the formula I and II are analogously prepared.

PRIOR ART

U.S. Pat. Nos. 3,690,810 and 3,817,995 describe hair coloring procedures in which hair is colored by oxidative coupling of certain preformed 5- or 7-hydroxy-1,4-benzothiazines with conventional primary intermediates such as p-toluenediamine or 2,5-diamino-4-methyl anisole to produce hair coloring pigments. This hair coloring technique requires the use of benzothiazine as a starting compound. The only oxidative agent specifically mentioned and illustrated is hydrogen peroxide.

DESCRIPTION OF THE INVENTION

The hair dyeing process of the present invention, comprises the preparation of an aqueous hair dyeing composition by oxidizing selected aminoethanethio substituted dihydroxybenzenes and an inorganic oxidant in an aqueous medium at a pH of from about 2 to 11. The composition is applied to the hair in such a manner that sufficient oxidation takes place in the hair to provide a tinctorially effective amount of hair coloring trichochrome, phaeomelanin or like pigment to permanently color the hair. The composition diffuses into the hair during the period of contact at a rate so that most of the pigment is formed in the hair and the hair is thereby permanently colored. The total contact time of the hair dyeing composition on the hair is normally less than one hour, typically from about 5 to 50 minutes, preferably 5 to 30 minutes.

By "permanent" is meant a color not removeable by shampooing with a conventional surfactant-containing shampoo, the permancency being attributable to the inability of the formed pigments to diffuse from the hair shaft in view of their molecular sizes.

By "applying" is meant contacting the hair to be dyed with a composition of the invention which is formed on the hair or just prior to contact with the hair, in a sufficient amount to effect a color change of the hair.

Trichochromes are polycyclic pigments generally characterized as yellow or red. Several of them are known and have been extracted from red hair and feathers under alkaline conditions.

Phaeomelanins are reddish-brown nitrogen and sulfur containing macromolecular pigments which are found in phaeomelanocytes. They are derived from tyrosinase oxidation of tyrosine and subsequent reaction with cysteine.

Trichochromes, phaeomelanins and like compounds are the end-product pigments of this invention. It is believed that these terms and their meanings are well understood by the skilled artisan even though the exact chemical identity of some of the products, particularly those formed by reaction of the intermediates formed during the oxidative process, with direct dyes, primary intermediates and/or couplers in accordance with the present invention is not precisely known or understood.

The aminoethanethio compounds used to form the oxidative compositions of this invention are shown below;

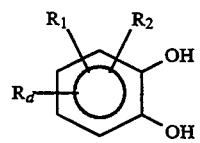

-continued

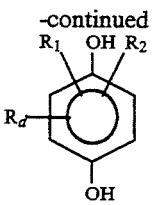
II wherein $R_1$ is

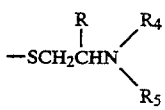

$R_d$ is

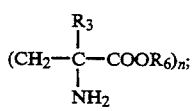

$R_2$, $R_3$, $R_4$ and $R_5$ which may be the same or different are each H, $C_1$-$C_6$ alkyl or $c_1$-$C_6$ hydroxyalkyl; R is H or $COOR_7$; $R_6$ and $R_7$ which may be the same or different are each alkali metal, H or $C_1$-$C_6$ alkyl, and n is 0 or 1.

The amount of substituted dihydroxybenzene which will be tinctorially effective depends upon many factors which can be readily evaluated by the skilled artisan either from experience or from a few simple tests. These factors include, for example, the color desired, the selected coloring agent or agents, the original color of the hair to be treated, the pH, auxiliary coloring agents employed, etc. Typically, however, the compositions of the invention will contain from about 0.1 to 10% percent by weight colorant, i.e., substituted dihydroxybenzene, preferably 0.1 to 2 percent.

All percents by weight defined in this specification and claims are percents by weight based on the total weight of the composition.

The oxidizing agents employed in this invention may be selected from periodate, iodate, persulfate and ferricyanide oxidizing agents including ammonium salts and salts of alkali metals, preferably sodium or potassium. The presently preferred oxidizing agent are sodium periodate and sodium iodate. Sodium salts are preferred because they are readily available and easily soluble in water. The selected oxidant will be employed in amounts sufficient to generate useful quantities of hair colorant. Typically it will vary from an approximate stoichiometric equivalent to a reasonable molar excess. The amount is not critical and will, of course, depend upon the oxidant selected.

Inasmuch as the pH of the reaction medium will vary during the reaction, it is desirable to provide a sufficient amount of a pH control agent in the reaction medium to maintain the requisite pH. In the process of the present invention, the preferable pH depends on the oxidant selected and on the dyeing procedure (one-step dyeing or two-step dyeing). Persulfates are usually optimal at an alkaline pH, while periodates and iodates can be used at a broad pH-range (pH 2-11). With periodate oxidant, the preferred pH range is pH 5-8. Ferricyanide is used at a pH 6-11, preferably 7-9.

Reagents for the control of pH in the compositions of this invention include various conventional buffers including those based on inorganic salts such as carbonates and bicarbonates. The pH control agents also include organic compounds widely employed in hair colorant compositions to maintain the desired pH. These include, for example, fatty acids especially long chain monocarboxylic or dicarboxylic acids such as dimer acid, linoleic acid or stearic acid in combination with amines such as ammonia, 2-amino-2-methyl propanol and monoethanol amine. Both types of reagents are referred to herein, and in the appended claims as pH control agents.

In the hair dyeing process of this invention, the selected aminoethanethio substituted dihydroxybenzene is applied to the hair in an aqueous composition at the selected pH in the presence of the selected oxidizing agent and maintained in contact with the hair for a sufficient period of time for a tinctorially effective amount of pigment to form. As aforesaid, most of the tinctorially effective pigment should form in the hair so that it elicits a permanent color change. It is believed that the substituted dihydroxybenzene molecule is sufficiently small so that it will migrate into the hair strand along with the oxidizing agent and the aqueous carrier. The trichochromes and phaeomelamins and like compounds that form, however, are such large molecules that they become trapped within the hair strand, thereby imparting the permanent color. It will be apparent that applying the hair dye composition to the hair after an appreciable amount of oxidation has taken place is not suitable since the pigments will not diffuse into the hair, and will be largely stripped away during subsequent shampooing.

The "contact time" as that term is employed herein is the period of time from the mixing of the reactants to the removal from the hair.

There are a number of variations in the procedure of this invention which can be employed to achieve the desired results. These include, for example, the one and the two step processes and the post oxidative process.

In the one step or simultaneous procedure, the mixture of hair colorant and oxidizing agent in aqueous medium at the selected pH are maintained in contact with the hair to be treated until sufficient oxidation products are formed to effect the desired result. The hair is then rinsed and dried.

In the two step or sequential process, the colorant in an aqueous medium at the selected pH, is applied to the hair and left for a period of from about 1 to 30 minutes preferably 10 to 20 minutes to permit the pigment precursor to migrate into the hair strand. A dilute aqueous solution of the oxidant is then brought into contact with the hair for another 1 to 20 minutes preferably 2 to 10 minutes until the desired coloration is attained. The hair is then rinsed and dried.

The post oxidative procedure is employed when a high degree of coloring is desired. It may be used following the one step process. The preferred oxidant is sodium periodate, but other oxidants may be employed. The essence of the procedure is that, after application of the one step process, the hair, preferably after rinsing, is again treated with an oxidant. The purpose of the post-oxidation treatment is to complete the conversion to useful pigment of any pigment precursor which may have migrated into the hair strand during the initial treatment but was not converted to a permanent coloring pigment. The process is illustrated in Example 36.

A further aspect of the present invention is the optional incorporation of a hair color modifier selected from the group consisting of one or more direct dyes, primary intermediate, coupler, cysteine and mixtures thereof in the oxidation mixture. Preferred modifiers include dihydroxyphenylalanine (dopa) or other dopa species, especially if the oxidizing agent is a ferricyanide. The process is illustrated in Example 35. It is believed that these components when present react at least in part with the intermediate compounds formed during pigment production thereby providing additional chromatic characteristics to the pigments ultimately obtained. When such color modifiers are employed, the amount of oxidant in the reaction mixture is increased to provide for the oxidation of these materials since some of them will be directly oxidized in the usual way rather than reacting with an intermediate of the primary reaction sequence. It will be apparent to the skilled artisan that by use of these auxiliary coloring agents, a wide variety tints, tones and shades can be achieved.

The term "dopa species" includes dopa itself as well as homologs, analogs and derivatives of dopa. It includes, for example cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group. The concentration of hair color modifier is normally less than about 10 mg/ml, and preferably is present in the reaction medium at from about 0.01 to about 5 mg/ml, most preferably from about 0.05 to about 2 mg/ml. The amount of these components should not be so great as to prevent the formation of the principal pigment. That is, the process of the present invention contemplates reaction of only a portion of the intermediate reaction products with the hair color modifiers.

A wide variety of direct dyes, primary intermediates and couplers are known to the skilled artisan and can be employed in this invention. The presently preferred primary intermediates and couplers include:

| | |
|---|---|
| Primary Intermediates: | p-phenylenediamine |
| | p-aminophenol |
| | o-aminophenol |
| | N,N-bis(2-hydroxyethyl)-p-phenylenediamine |
| | 2,5-diaminopyridine |
| | p-toluenediamine |
| Couplers: | resorcinol |
| | m-aminophenol |
| | α-naphthol |
| | 5-amino-o-cresol |
| | 2-methylresorcinol |
| | N-acetyl dopa |
| | 4,6-di(hydroxyethoxy)-m-phenylenediamine |
| | m-phenylenediamine |

Suitable direct dyes include, for example, nitro dyes, azo dyes and anthraquinone dyes.

Another optional modifier which can be employed in the process of this invention is the amino acid cysteine. The use of this compound is illustrated in Examples 19 through 23 below. It is used at substantially the same concentration as other modifiers to achieve desirable hair colors. The exact mechanism by which cysteine operates is not known. It probably substitutes on the benzene ring through a thio group.

The variously described embodiments of the present invention may also include in the hair dye composition one or more optional ingredients, which may be provided in one or more additional containers of the kits to be described in more detail hereinafter for admixture by the user into the aqueous reaction mixture, or, if compatible, may be incorporated into the oxidant or colorant premix solutions described previously.

Such ingredients include well-known conventional additives usually employed in oxidative hair coloring compositions such as organic solvents, thickeners, surface-active agents to assist in penetration of the hair shaft, pH adjusting agents, antioxidants, fragrances and chelating agents.

The hair dye compositions used in the process of the present invention can include an organic solvent as a cosolvent. The organic solvent may assist in the dissolution of the components of the composition, and is present typically in an amount up to about 30%, preferably up to about 15%. A desirable range is from about 0.1 to about 15%, most preferably from about 1 to 10%. Suitable solvents are mono- and polyhydric alcohols, for example, ethyl alcohol, isopropyl alcohol, propylene glycol, benzyl alcohol, etc., and glycol ethers, such as 2-butoxyethanol, ethylene glycol monoethyl ether and diethyleneglycol monoethyl ether. The cosolvent is one that is only minimally oxidized by the oxidant or, preferably, oxidation resistant.

Surface-active agents employed in the dyeing compositions of this invention can be anionic, nonionic, cationic, amphoteric or zwitterionic. By way of examples of the various types of surface-active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate; glyceryl monostearate; triethanolamine oleate, sodium salt of palmitic methyl taurine; cetyl pyridinium chloride; lauryl sulfonate; myristyl sulfonate, lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylaphthalene sodium sulfonate; dioctyl sodium sulfonsuccinate; sodium N-methyl-N-oleoyl taurate; oleic acid ester of sodium isothionate; sodium dodecyl sulfate; the sodium salt of 3-diethyl tridecanol-6-sulfate and the like. The quantity of surface-active agent can vary over a wide range, such as from about 0.05% to 15% and preferably from about 0.10 to 5% by weight of the composition. The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

Chelating and sequestering agents include, for example, ethylenediaminetetraacetic acid, sodium citrate, etc., and, if used, may be present in an amount of under about 1%.

A thickening agent may also be incorporated in the dyeing composition of this invention, which may be one or several of those commonly used in hair dyeing. These are exemplified by such products as sodium alginate or gum arabic, or cellulose derivatives, such as methylcellulose, e.g., Methocel 60HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.1 to 5% by weight of the composition. The viscosity of the composition may vary from about 1 cp to about 100,00 cps. For a typical lotion formulation, composition viscosity is between about 100 cps to about 10,000 cps, at which viscosity the composition can be applied to the hair without running or dripping.

The list of optional ingredients is not intended as limiting. Other suitable adjuvants for inclusion in the hair dye composition are recited, for example, in Zviak, *The Science of Hair Care* (1986) and Balsam and Sagarin, *Cosmetics: Science and Technology*, Vol. 2 (Second Edition 1972).

The process of the present invention may conveniently be practiced by providing premeasured amounts of the reactants in separate containers packaged in kit form. The user simply admixes the reactants for application to the hair in accordance with the selected practice of the invention. It will be apparent that no special expertise is required to carry out the process, and accordingly the product and process are equally suitable for in-home use by the nonprofessional as well as salon use by the professional. Advantageously, the product in kit form is shelf-stable and is therefore suitable for retail sale without precautions required for some hair clorant compositions, e.g., storage under anaerobic conditions.

The kit provided in accordance with this aspect of the invention comprises a first container containing the oxidizable colorant and a second container containing the oxidant. The buffer may be individually packaged in a third container, or it may be present in the first or second container. Selected modifiers may be mixed with the basic hair colorant of the invention or may be in separate containers.

While the kit may include packets containing amounts, preferably premeasured, of dry powders for preparation of these solutions, it is more convenient to provide them as solutions. Moreover, solutions containing premeasured quantities of the constituents facilitates their correct use by the consumer.

One or more additional containers containing the optional constituents may be provided in the kit. The optional constituents may also be contained within the solutions of the previously described containers, barring any incompatibility.

The consumer admixes the components of the kit, suitably as the aqueous solutions or as dry powders and water, according to written instructions, to obtain the aqueous reaction mixture. Mixing may be conducted in a separate vessel supplied with or external to the kit, or may take place in a container of the kit adapted to provide sufficient head space for mixing. The reactants may also be admixed on the hair of the user. Reaction commences upon mixing. The hair colorant will subsequently oxidize as described herein whereby a permanent hair color is obtained. After the desired hair shade is reached, most preferably within about 30 minutes, the hair dye composition that was applied to the hair is removed, preferably with a conventional shampoo.

The following non-limiting examples are given by way of illustration only.

In the examples, the colors are evaluated utilizing the standard Hunter Tristimulus values. In the Hunter method, the parameters a and b may be positive or negative and define the chromatic condition of the hair. Thus, the more positive the a value, the greater the redness of the hair, while a negative a value indicates greenness. Similarly, positive b values indicate yellowness, while negative b values indicate blueness. The L parameter is a measure of color itnensity, and has a value of 0 for absolute black to 100 for absolute white. Generally, hair having an L value of about 15 or less is considered black, while an L value of about 60 is white. It should be understood that the L value scale is not linear, but rather is sigmoidal. Proximate to 0 and proximate to 100 hair color intensity apparent to the human eye varies minimally with unit changes in the L value. Between values of about 20 to about 50, hair color intensity varies significantly with unit changes in L value. Thus, the Hunter values are more sensitive in the region where the human eye is able to perceive color changes.

EXAMPLES 1-31

The following table shows the successful results achieved with the compositions and methods of this invention utilizing the following compounds:

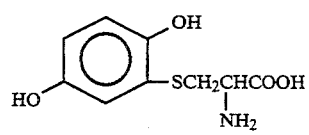
A

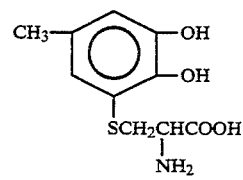
B

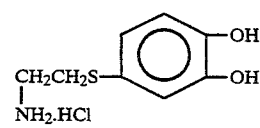
C

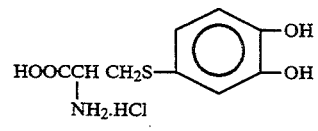
D

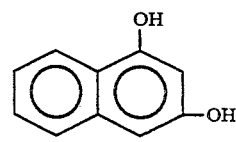
E

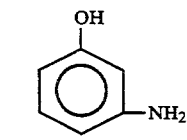
F

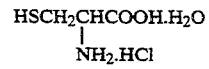
G

TABLE

| Entry | Dyes | [%] | pH | Dyeing Method | hair | Hunter Tr. Values L | a | b | color |
|---|---|---|---|---|---|---|---|---|---|
| 1 | A | 0.7 | 7.5 | 2-step | gr | 30.4 | 0.5 | 6.6 | gray |
| 2 | A | 0.7 | 7.5 | 2-step | bl | 39.1 | 0.2 | 9.5 | lt gray-brown |
| 3 | A | 0.7 | 7.5 | 1-step | bl | 52.0 | 7.7 | 17.2 | lt red-brown |
| 4 | A | 0.7 | 9.7 | 2-step | gr | 30.8 | 0.6 | 7.2 | gray brown |
| 5 | A | 0.7 | 7.7 | 2-step | bl | 28.8 | 3.0 | 9.3 | brown |
| 6 | A | 0.4 | 7.7 | 1-step | bl | 36.9 | 11.8 | 16.4 | orange-brown |
| 7 | B | 0.7 | 7.7 | 2-step | gr | 30.3 | 0.5 | 8.5 | gray |
| 8 | B | 0.7 | 7.7 | 2-step | bl | 53.0 | 2.7 | 18.6 | blonde |
| 9 | B | 0.7 | 9.5 | 2-step | gr | 30.7 | 0.2 | 9.7 | gray-yellow |
| 10 | B | 0.7 | 9.5 | 2-step | bl | 44.2 | 1.6 | 20.1 | blonde |
| 11 | B | 0.4 | 7.7 | 1-step | bl | 45.6 | 10.5 | 19.3 | orange-blonde |
| 12 | B E | 0.5 0.25 | 9.9 | 2-step | gr | 32.5 | 1.9 | 8.8 | gray-orange |
| 13 | B E | 0.5 0.25 | 9.9 | 2-step | bl | 46.5 | 8.7 | 21.9 | orange-blonde |
| 14 | C | 0.3 | 7.5 | 2-step | gr | 27.6 | 1.5 | 5.8 | brown |
| 15 | C | 0.3 | 7.5 | 2-step | bl | 29.1 | 3.6 | 7.0 | brown |
| 16 | C F | 0.4 0.2 | 7.9 | 2-step | gr | 23.6 | 2.4 | 5.6 | chestn. brown |
| 17 | C F | 0.4 0.2 | 7.9 | 2-step | bl | 22.5 | 4.3 | 7.3 | chestn. brown |
| 18 | C F | 0.4 0.2 | 7.6 | 1-step | bl | 39.5 | 5.5 | 10.9 | lt brown |
| 19 | C G | 0.4 0.25 | 7.1 | 2-step no heat | gr | 27.7 | 0.5 | 5.9 | brown-gray |
| 20 | C G | 0.4 0.25 | 7.1 | 2-step | gr | 24.6 | 2.3 | 5.7 | red-brown |
| 21 | C G | 0.4 0.25 | 7.1 | 2-step no heat | bl | 26.2 | 0.2 | 3.6 | gray-brown |
| 22 | C G | 0.4 0.25 | 7.1 | 2-step | bl | 26.2 | 6.5 | 5.9 | brown-violet |
| 23 | C G | 0.2 0.15 | 7.1 | 1-step | bl | 30.1 | 8.4 | 7.0 | brown-violet |
| 24 | C E | 0.5 0.25 | 7.1 | 2-step | gr | 22.1 | 0.4 | 6.7 | dk gray-brown |
| 25 | C E | 0.5 0.25 | 7.1 | 2-step | bl | 17.0 | 1.3 | 5.0 | dk brown |
| 26 | D | 0.5 | 8.7 | 2-step | gr | 29.3 | 2.9 | 5.7 | gray-brn |
| 27 | D | 0.5 | 8.7 | 2-step | bl | 31.4 | 7.6 | 5.7 | brown-violet |
| 28 | D F | 0.5 0.26 | 8.5 | 2-step | gr | 30.6 | 2.5 | 6.4 | gray-brown |
| 29 | D F | 0.5 0.26 | 8.5 | 2-step | bl | 28.3 | 4.3 | 9.5 | med. brown |
| 30 | D G | 0.5 0.26 | 8.9 | 2-step | gr | 31.4 | 2.9 | 6.1 | gray-brown |
| 31 | D | 0.5 | 8.9 | 2-step | bl | 33.9 | 8.4 | 6.7 | brown-violet | undyed hair:
bleached L 70.3 a −0.5 b 18.7
gray L 35.8 a 0.7 b 5.2
2-step dyeing was performed as follows:
An aqueous solution of the coloring agent was prepared at the concentration shown in the table and the pH was adjusted to the specified value with NaHCO$_3$ or monoethanolamine. The solution was applied to hair and left for 10 minutes and the hair was contacted with a 1% aqueous solution of sodium periodate for 5 minutes, rinsed and dried.
1-step dyeing was performed as follows:
Aqueous solutions containing the coloring agent (concentration see Table) and sodium periodate (0.4%) at the specified pH adjusted as in the 2-step process (see Table). Hair was contacted with the composition for 10 minutes, rinsed and dried.
In Examples 12, 13, 16–25, 28–30, the identified modifier was added as an auxiliary coloring agent. If used in a 2-step process, the modifier was present in the first solution applied to hair.

EXAMPLE 32

20 mg 4-S-cysteaminylcatechol hydrochloride (0.09 mmole of compound C from examples 1–31) and 18 mg sodium iodate (0.09 mmole) were dissolved in 5 ml water. The solution was applied to white hair and left for 10 minutes. The pH of the solution was about 4.5 at the beginning and about 5.0 at the end of the treatment. The hair was rinsed and dried with heat (hairdryer). The hair was dyed to a light reddish brown color.
Hunter Tr. Val. before: L 70.3 a −0.5 b 18.7
Hunter Tr. Val. after: L 35.1 a 8.7 b 6.1 reddish brown

EXAMPLE 33

20 mg 4-S-cysteaminylcatechol hydrochloride (0.09 mmole), 59 mg potassium ferricyanide (0.18 mmole) and 35 mg sodium bicarbonate were dissolved in 5 ml water. The pH of the solution was about 7.6. The solution was applied to white hair and left for 10 minutes. The hair was rinsed and dried with heat (hairdryer). The hair was dyed to an auburn color.
Hunter Tr. Val. 24.8 a 8.7 b 4.9 auburn

EXAMPLE 34

20 mg 4-S-cysteaminylcatechol hydrochloride (0.09 mmole), 21 mg sodium persulfate (0.09 mmole) and 35 mg sodium bicarbonate were dissolved in 5 ml water. The pH of the solution was about 7.6. The solution was applied to white hair and left for 10 minutes. The hair was rinsed and dried with heat (hairdryer). The hair was dyed to a light red-brown color.

Hunter Tr. Val. L 35.0 a 11.7 b 7.3 red-brown

EXAMPLE 35

10 mg 4-S-cysteaminylcatechol hydrochloride (0.045 mmole), 9 mg dopa (0.045 mmole), 59 mg potassium ferricyanide and 35 mg sodium bicarbonate were dissolved in 5 ml water. The pH was about 7.8. The solution was applied to white hair and left for 20 minutes. The hair was rinsed and dried with heat (hairdryer). The hair was dyed to a reddish brown color.

Hunter Tr. Val. L 27.5 a 8.6 b 6.3 reddish brown

EXAMPLE 36

A swatch of white hair was treated exactly as in Example 35 with the exception that after rinsing and before drying the hair was exposed to an aqueous solution of 1% sodium periodate for 2 minutes. After drying with heat (hairdryer), the hair had a warm brown color.

Hunter Tr. Val. L 23.3 a 5.6 b 6.5 warm brown

EXAMPLE 37

20 mg 4-S-cysteaminylcatechol-hydrochloride (0.09 mmole), 36 mg sodium iodate (0.18 mmole) and 10 mg sodium bicarbonate were dissolved in 5 ml water. The pH of the solution was 7.2 White hair was treated with this solution for 10 minutes, rinsed with water and dried with a hair-dryer. The hair was dyed to a mahogany color.

|  | L | a | b |
|---|---|---|---|
| Hunter Tr. val. before dyeing: | 67.1 | −0.6 | 18.5 |
| Hunter Tr. val. after dyeing | 35.4 | 11.2 | 7.7 |

What is claimed:

1. A method of permanently coloring hair comprising the steps of:
   (a) applying to the hair an aqueous oxidizing composition having a pH of from about 2 to 11 and containing (i) a tinctorially effective amount of an aminoethanethio substituted dihydroxybenzene having a structure set forth below:

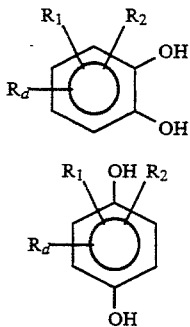

wherein $R_1$ is

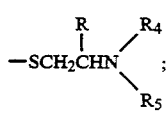

$R_d$ is

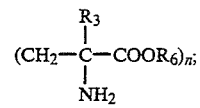

R is H or $COOR_7$;

$R_2$, $R_3$, $R_4$ and $R_5$, which may be the same or different, are H, $C_1$–$C_6$ alkyl or $C_1$–$C_6$ hydroxyalkyl; $R_6$ and $R_7$, which may be the same or different, are alkali metal, H or $C_1$–$C_6$ alkyl, and n is 0 or 1, and (ii) a periodate, iodate, ferricyanide or persulfate oxidizing agent, and (b) permanently coloring the hair by allowing the composition to remain in the hair to achieve the desired color by the formation of phacomelanins or trichochromes in the hair.

2. The method of claim 1 wherein the composition further comprises a color modifier selected from the group consisting of direct dyes, primary intermediates, couplers, cysteine, dopa species selected from the group consisting of dopa, $C_1$ to $C_4$ alpha alkyl dopa, epinephrine, $C_1$ to $C_6$ alkyl esters of dopa, and mixtures thereof.

3. The method of claim 1 wherein the oxidizing composition is formed on the hair by sequential addition of the aminoethanethio substituted dihydroxybenzene and the oxidizing agent.

4. The method of claim 1 wherein the oxidizing composition is formed on the hair by simultaneous addition of the aminoethanethio substituted dihydroxybenzene and the oxidizing agent.

5. The method of claim 3 wherein the oxidizing agent is sodium periodate.

6. The method of claim 4 wherein the oxidizing agent is sodium periodate.

7. The method of claim 4 further comprising a post-oxidative step with an oxidizing agent.

8. An aqueous composition for permanently dyeing hair comprising (a) a tinctorially effective amount of an aminoethanethio substituted dihydroxybenzene having a structure set forth below:

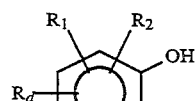

wherein $R_1$ is

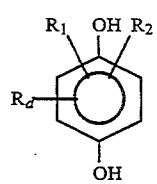

$R_d$ is

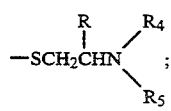

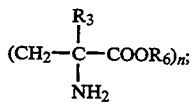

R is H or COOR$_7$;

R$_2$, R$_3$, R$_4$ and R$_5$, which may be the same or different, are H, C$_1$–C$_6$ alkyl or C$_1$–C$_6$ hydroxyalkyl; R$_6$ or R$_7$, which may be the same or different, are alkali metal, H or C$_1$–C$_6$ alkyl, and n is 0 or 1, and (b) a periodate, iodate, ferricyanide or persulfate oxidizing agent, said aminoethanthio substituted dihydroxybenzene being oxidizable by said oxidant to form phaeomelanins, or trichochromes.

9. The composition of claim 8 further comprising a color modifier selected from the group consisting of direct dyes, primary intermediates, couplers, cysteine, dopa species selected from the group consisting of dopa, C$_1$ to C$_4$ alpha alkyl dopa, epinephrine, C$_1$ to C$_6$ alkyl esters of dopa, and mixtures thereof.

10. The composition of claim 8 wherein the oxidizing agent is sodium periodate.

11. A hair dyeing kit for permanently dyeing hair having in a single package a plurality of containers, the kit comprising (a) a first container containing a tinctorially effective amount of an aminoethanthio substituted dihydroxybenzene having a structure set forth below:

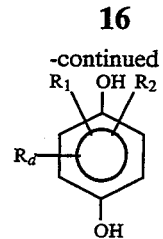  I

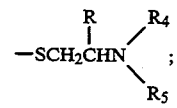

wherein R$_1$ is

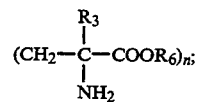

R$_d$ is

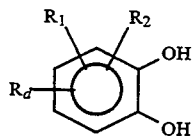

R is H or COOR$_7$; R$_2$, R$_3$, R$_4$ and R$_5$, which may be the same or different, are H, C$_1$–C$_6$ alkyl or C$_1$–C$_6$ hydroxyalkyl; R$_6$ or R$_7$, which may be the same or different, are alkali meta, H or C$_1$–C$_6$ alkyl, and n is 0 or 1, and (b) a second container containing a periodate, iodate, ferricyanide or persulfate oxidizing agent, there being present in any one of said first container or said second container or in a third container a pH control agent, the amount of said pH control agent contained in the kit being sufficient to provide a pH of from about 2 to 11 when the contents of the first and second containers or of the first, second and third containers are mixed, the amounts of the aminoethanthio substituted dihydroxybenzene and oxidant in the kit being sufficient to effect such permanent dyeing of hair when the contents of the containers are mixed and applied to the hair.

12. The hair dyeing kit of claim 11 further comprising, in a container other than the container containing the oxidizing agent, a color modifier selected from the group consisting of direct dyes, primary intermediates, cysteine, dopa species selected from the group consisting of dopa, epinephrine, C$_1$ to C$_4$ alpha alkyl dopa, C$_1$ to C$_6$ alkyl esters of dopa, and mixtures thereof.

13. The kit of claim 11 wherein the oxidizing agent is sodium periodate.

* * * * *